US012121714B2

(12) United States Patent
Esquenazi (10) Patent No.: US 12,121,714 B2
(45) Date of Patent: Oct. 22, 2024

(54) SEWING RING WITH QUICK CONNECT TO INFLOW

(71) Applicant: HeartWare, Inc., Miami Lakes, FL (US)

(72) Inventor: Paul Esquenazi, Hialeah, FL (US)

(73) Assignee: HeartWare, Inc., Miami Lakes, FL (US)

( * ) Notice: Subject to any disclaimer, the term of this patent is extended or adjusted under 35 U.S.C. 154(b) by 359 days.

(21) Appl. No.: 17/246,782

(22) Filed: May 3, 2021

(65) Prior Publication Data

US 2021/0339007 A1 Nov. 4, 2021

Related U.S. Application Data

(60) Provisional application No. 63/019,512, filed on May 4, 2020.

(51) Int. Cl.
| | | |
|---|---|---|
| A61M 60/863 | (2021.01) | |
| A61M 60/178 | (2021.01) | |
| A61M 60/859 | (2021.01) | |
| A61M 60/216 | (2021.01) | |
| A61M 60/81 | (2021.01) | |
| A61M 60/861 | (2021.01) | |
| A61M 60/894 | (2021.01) | |

(52) U.S. Cl.
CPC ........ *A61M 60/863* (2021.01); *A61M 60/178* (2021.01); *A61M 60/859* (2021.01); *A61M 60/216* (2021.01); *A61M 60/81* (2021.01); *A61M 60/861* (2021.01); *A61M 60/894* (2021.01)

(58) Field of Classification Search
CPC .............. A61M 60/861; A61M 60/894; A61M 60/216; A61M 60/859; A61M 60/81; A61M 60/178; A61M 60/863
See application file for complete search history.

(56) References Cited

U.S. PATENT DOCUMENTS

| | | |
|---|---|---|
| 5,322,518 A | 6/1994 | Schneider et al. |
| 5,702,430 A | 12/1997 | Larson, Jr. et al. |
| 5,968,082 A | 10/1999 | Heil |
| 9,981,077 B2 | 5/2018 | Callaway et al. |
| 2002/0129470 A1* | 9/2002 | Kiely ..................... A44B 19/38 24/433 |
| 2004/0002624 A1* | 1/2004 | Yu ....................... A61M 60/827 600/16 |

(Continued)

OTHER PUBLICATIONS

International Search Report and Written Opinion dated Jul. 9, 2021, for corresponding International Application No. PCT/US2021/1030394, International Filing Date: May 3, 2021 consisting of 11-pages.

*Primary Examiner* — Pamela M. Bays
(74) *Attorney, Agent, or Firm* — Shumaker & Sieffert, P.A.

(57) ABSTRACT

The present invention relates to an attachment device having a sewing ring frame and a locking element mounted on the sewing ring frame. The locking mechanism includes a flange element projecting from the outer surface of the sewing ring frame and a retractable locking pin projecting towards the interior of the sewing ring frame. The flange is coupled to the locking pin and the biasing element. The locking mechanism is transitionable between a locked configuration in which the locking pin is in an engaged position to an unlocked configuration in which the locking pin is in a disengaged position.

20 Claims, 6 Drawing Sheets

(56) References Cited

U.S. PATENT DOCUMENTS

| | | | |
|---|---|---|---|
| 2017/0266358 A1* | 9/2017 | Aber | A61M 60/419 |
| 2018/0050143 A1* | 2/2018 | Nguyen | A61M 60/863 |
| 2019/0038819 A1* | 2/2019 | Arslan | A61M 60/863 |

* cited by examiner

SEWING RING WITH QUICK CONNECT TO INFLOW

CROSS-REFERENCE TO RELATED APPLICATION

This application claims the benefit of U.S. Application Ser. No. 63/019,512 FILED May 4, 2020.

TECHNICAL FIELD

The present technology is generally related to blood pumps and associated devices for intracardiac attachment.

BACKGROUND

Blood pumps, such as a ventricular assist devices ("VAD"), are used to help pump blood from the lower chambers of the heart throughout the body. VADs are most commonly used in people who have weakened hearts or heart failure. VADs are often implanted in patients waiting for a heart transplant or as treatment for a patient's heart to become strong enough to effectively pump blood throughout the body on its own. A Left Ventricular Assist Device (LVAD) is a particular type of blood pump implanted into the apex of a patient's heart during a surgery that receives blood from the left ventricle and pumps the blood to the patient's aorta and throughout the entire body.

Implanting a VAD often requires a hole or cavity to first be "cored" in the myocardium so that a portion of the VAD may be inserted into the apex of the left or right ventricle of the heart. Before the VAD is inserted into the heart, a sewing ring may be sewn, stitched, or otherwise mounted onto the myocardium so that a housing unit of the VAD is not in direct contact with the myocardial tissue. The attachment of a sewing ring also allows for pump orientation adjustments. Once the sewing ring is mounted on the myocardial tissue, an inflow cannula of the VAD may then be inserted into the left or right ventricle through the cored hole. The VAD then pumps the patient's blood back into circulation through an outflow cannula that may be grafted into the aorta.

Techniques have been developed which are used to implant the blood pumps into the heart. Known sewing rings utilize tools such as screwdrivers, wrenches, and the like.

SUMMARY

The present invention advantageously provides a toolless system for attaching a ventricular assist device (VAD) to a patient's heart during a surgical procedure. In one exemplary embodiment, the system includes an attachment device having a sewing ring frame and a locking mechanism. The sewing ring frame has a first surface, a second surface, an inner surface, and an outer perimeter. The locking mechanism is mounted on the first surface of sewing ring frame. The inner surface of the sewing ring frame defines an aperture sized to receive an inflow cannula of an implantable blood pump. The locking mechanism further includes a flange proximate to the outer perimeter of the sewing ring frame, a locking pin proximate to the aperture and distal to the flange, and a biasing element disposed between the flange and the locking pin. The flange is coupled to the biasing element and the locking pin and projects from the outer perimeter of the sewing ring frame. The locking pin projects from the inner surface of the sewing ring frame towards the aperture. The locking mechanism is further configured to transition between an engaged locked configuration to a disengaged unlocked configuration when a pulling force is applied to the flange.

In one embodiment, the sewing ring frame includes at least one slot.

In another embodiment, the biasing element is a spring.

In another embodiment, the locking pin projects from the inner surface of the sewing ring frame when the locking mechanism is in the locked configuration.

In another embodiment, the locking pin is retracted towards the biasing element and the flange when the locking mechanism is in the unlocked configuration.

In another embodiment, the attachment device is an apical attachment device.

In another embodiment, the sewing ring frame is made up of a bio-compatible material.

In yet another embodiment, an implantable blood pump system includes an apical attachment device having a sewing ring frame, the sewing ring frame having a first surface, a second surface, an inner surface, and an outer perimeter. The inner surface defines an aperture sized to receive an inflow cannula of an implantable blood pump. The apical attachment device further includes a locking mechanism mounted to the first surface of the sewing ring frame, the locking mechanism having a flange proximate to the outer surface, a locking pin proximate to the aperture and distal to the flange, and a biasing element disposed between the flange and locking pin. The flange may be coupled to the biasing element and the locking pin and projects from the outer perimeter of the sewing ring frame. The locking pin projects from the inner surface towards the aperture. The implantable blood pump system further includes an implantable blood pump having the inflow cannula and an attachment ring. The inflow cannula has a proximal portion and a distal portion, the attachment ring is disposed on the proximal portion of the inflow cannula and includes a corresponding mating member configured to be readily engaged by the locking pin to secure the implantable blood pump to the apical attachment device.

In another embodiment, the sewing ring frame includes at least one slot.

In another embodiment, the biasing element is a spring.

In another embodiment, the corresponding mating member is at least one detent.

In another embodiment, the at least one detent is circumferentially disposed around the attachment ring.

In another embodiment, the locking pin is configured to directly engage the at least one detent.

In another embodiment, the locking pin projects from the inner surface of the sewing ring frame towards the aperture when the locking mechanism is in an engaged locked configuration.

In another embodiment, the locking pin is retracted towards the biasing element and the flange when the locking mechanism is in a disengaged unlocked configuration.

In another embodiment, the locking mechanism is configured to be transitionable between the engaged locked configuration and the disengaged unlocked configuration.

In another embodiment, the locking mechanism is transitionable from the engaged locked configuration to the disengaged unlocked configuration when a pulling force is applied to the flange.

In another embodiment, the engagement of the locking pin to the at least one detent prevents rotational and axial displacement of the implantable blood pump when the attachment device is affixed to the implantable blood pump.

In another embodiment, the implantable blood pump is a Left Ventricular Assist Device (LVAD).

In yet another embodiment, a system for attaching an apical attachment device to a Left Ventricular Assist Device (LVAD) includes an attachment device having a sewing ring frame and a locking mechanism. The sewing ring frame having a first surface, a second surface, an inner surface, and an outer perimeter, the inner surface defining an aperture sized to receive an inflow cannula of the LVAD. The locking mechanism includes a flange proximate to the outer perimeter, a locking pin proximate to the aperture and distal to the flange, and a spring biasing element disposed between the flange and the locking pin. The flange is coupled to the biasing element and the locking pin, and projects from the outer perimeter of the sewing ring frame. The locking mechanism is configured to transition between an engaged locked position to a disengaged unlocked configuration when a pulling force is applied to the flange. The system for attaching an apical attachment device to an LVAD further includes an LVAD having an inflow cannula and an attachment ring. The inflow cannula has a proximal portion and a distal portion. The attachment ring has a first surface and is attached to the proximal portion of the inflow cannula. The attachment ring further includes at least one detent circumferentially disposed around the first surface. The locking pin of the locking mechanism is configured to lockingly engage at least one of the at least one detent to secure the LVAD to the apical attachment device, the engagement of the locking pin and the at least one detent prevents rotational displacement of the LVAD.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

One aspect of the present disclosure addresses the above-mentioned needs. Although the embodiments and examples of the invention are described in the context of a tool-less system for connecting an implantable blood pump to the heart, descriptions of the invention in this context are not intended to be limiting in any way.

As used herein, relational terms, such as "first" and "second," "inner" and "outer", and the like, may be used solely to distinguish one entity or element from another entity or element without necessarily requiring or implying any physical or logical relationship or order between such entities or elements.

Figure 1:
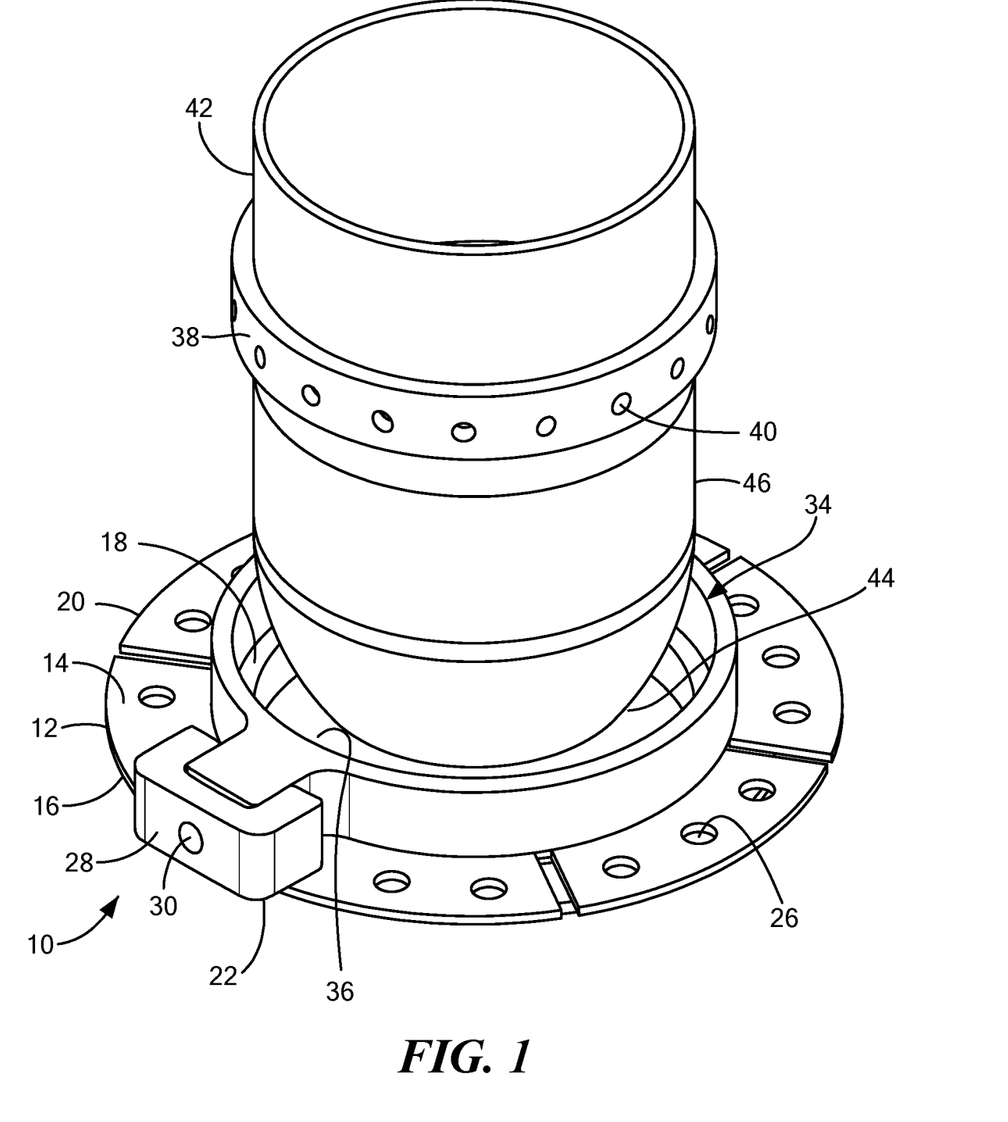
FIG. 1 is a side view illustrating an attachment device in accordance with the invention, wherein the attachment device is engaged by the inflow cannula of a blood pump.
Figure 3:
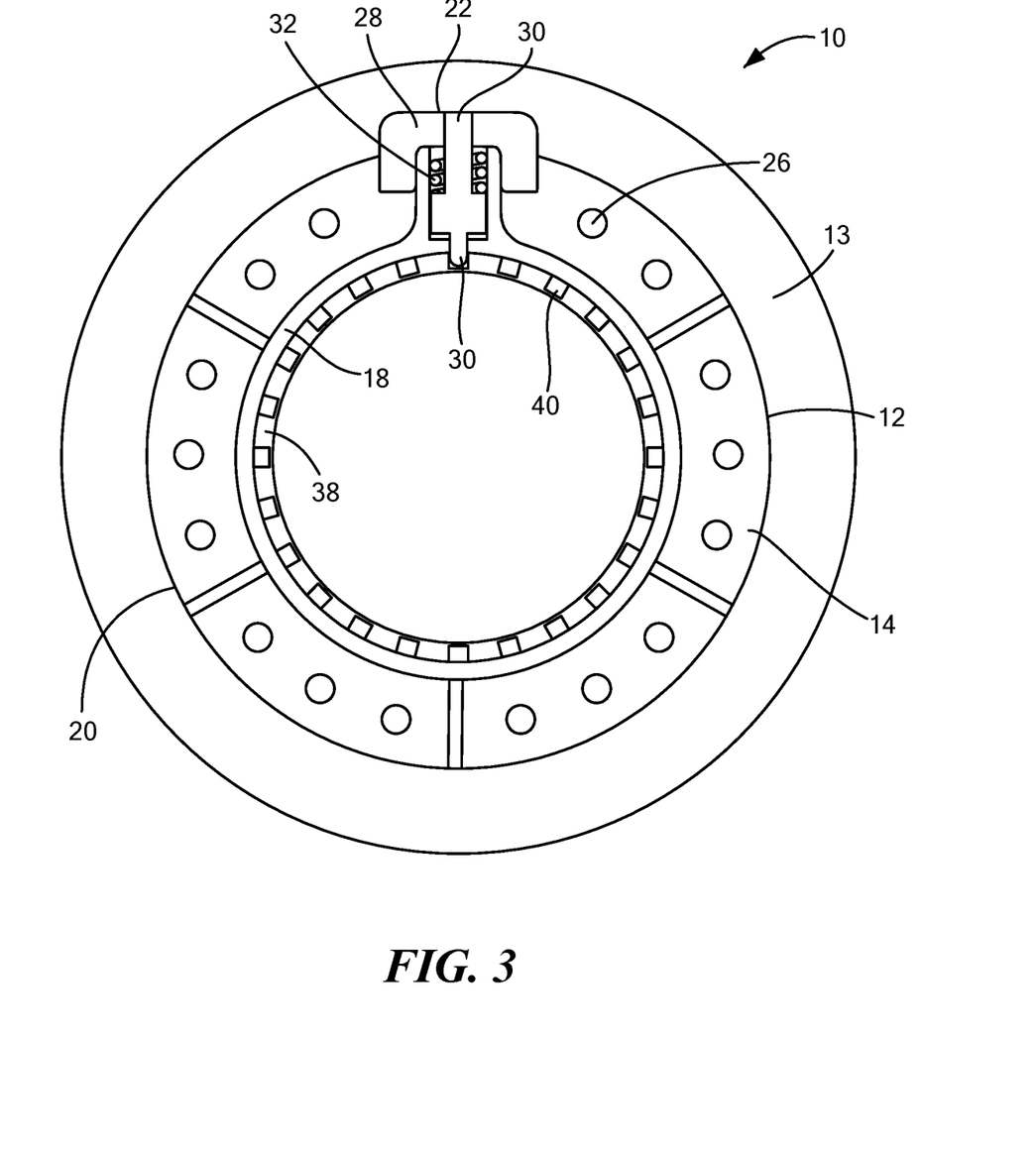
FIG. 3 is a top view of the invention of FIG. 1, wherein the locking mechanism is in a locked state and is releasably attached to an inflow ring of the blood pump.
Figure 6:
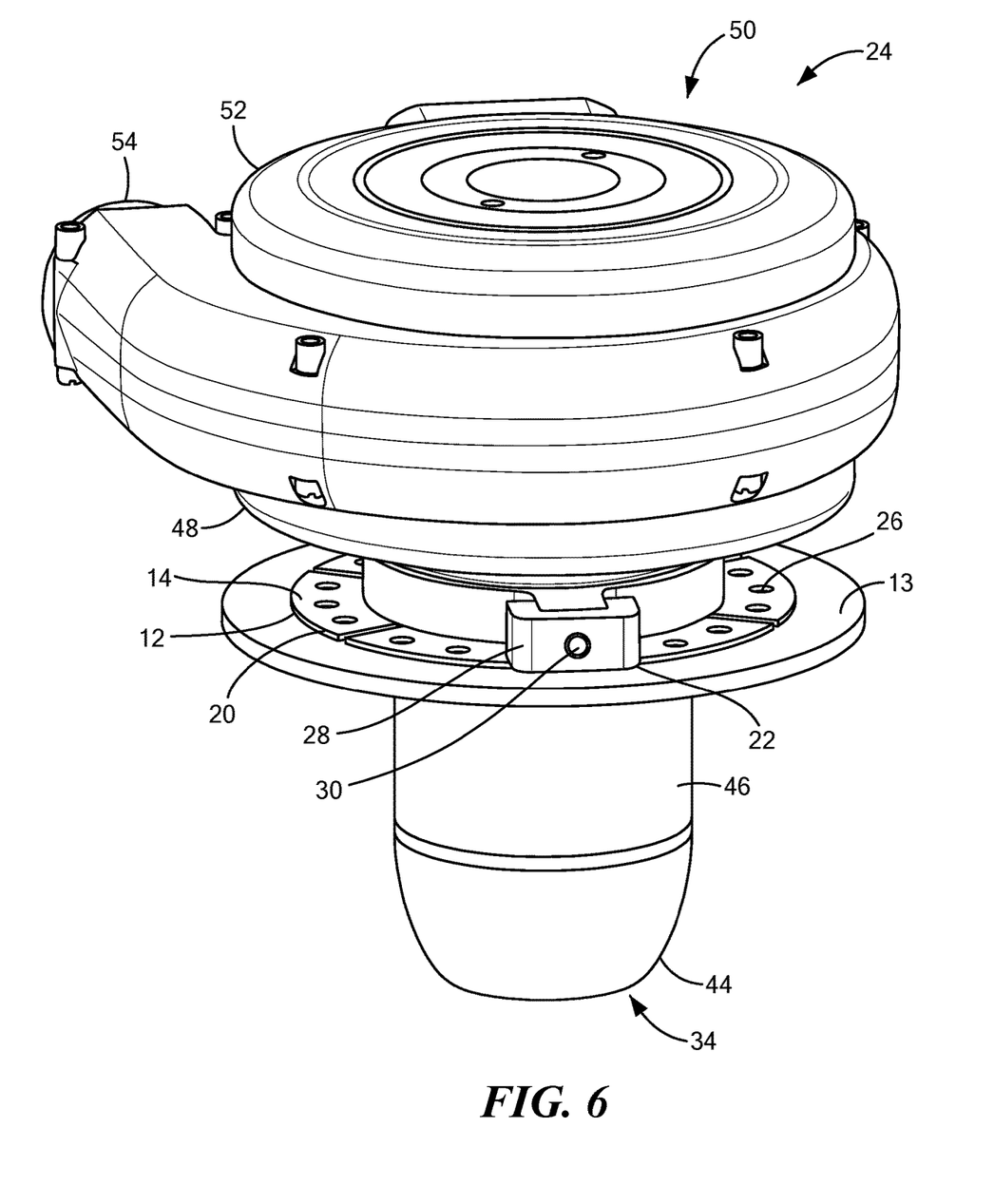
FIG. 6 is a side view of the invention of FIG. 1 illustrating the completed attachment of the VAD and the attachment device.

Now referring to the drawings in which like reference designators refer to like elements, there is shown in FIG. 1 an attachment device for coupling a blood pump to the heart of a patient and designated generally as "10". The attachment device 10 includes a sewing ring frame 12 and may be attached to a suturing ring 13 (as shown in FIGS. 3 and 6). The sewing ring frame 12 includes a first surface 14, a second surface 16, an inner surface 18, and an outer perimeter 20. A locking mechanism 22 is disposed on the first surface 14 to assist a user, such as a clinician, in attaching an implantable blood 24 pump to the myocardial tissue of a patient's heart. In the illustrated embodiment, the sewing ring frame 12 may include at least one hole or slot 26 so that the attachment device 10 may be stitched, sutured, sewn, mounted, or otherwise adhered to the myocardial tissue of the heart to prevent displacement of the attachment device once inserted into the patient's body. The sewing ring frame 12 and locking mechanism 22 may be made up of metal, fabric, or any other biocompatible material.

Figure 2:
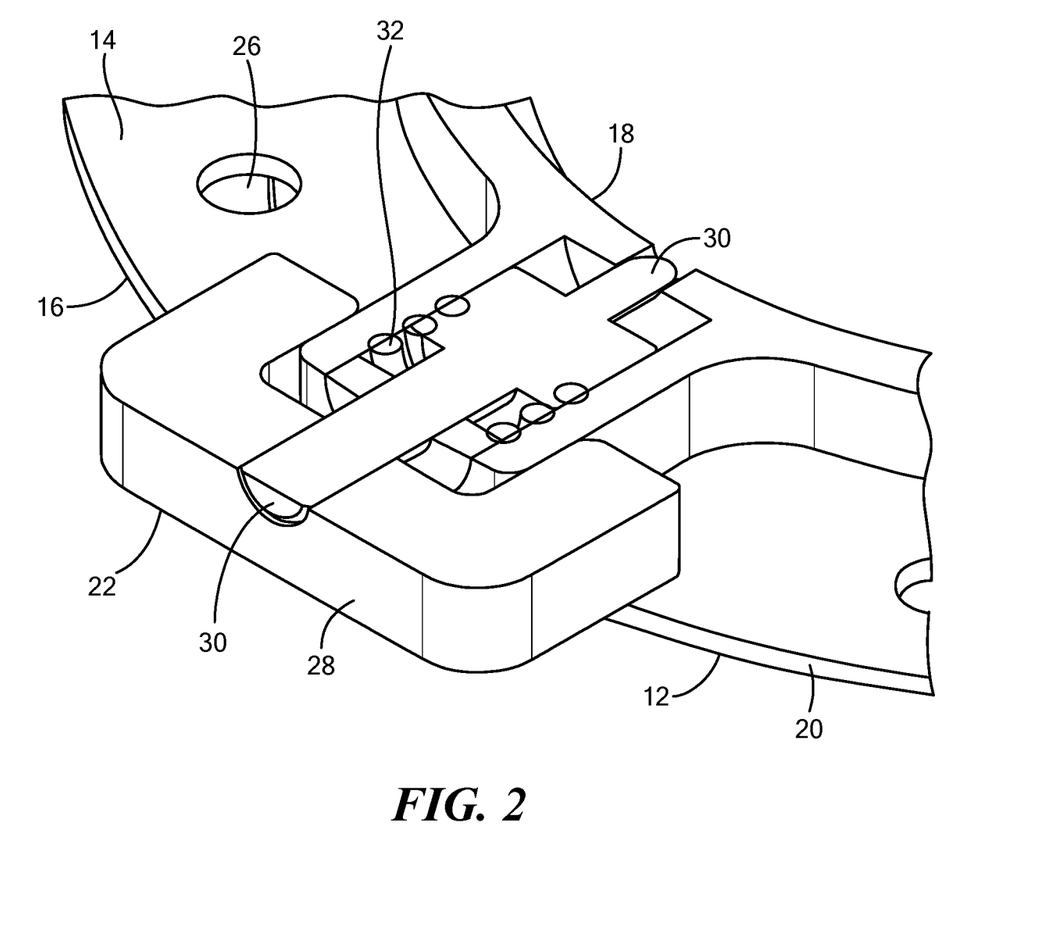
FIG. 2 is a perspective view illustrating the invention of FIG. 1, wherein the locking mechanism of the attachment device is in an unlocked state and may be releasably attached to a blood pump to supplement the function of the heart in pumping blood to the body in accordance with an embodiment of the invention.

Referring now to FIG. 2, the locking mechanism 22 may be mounted or otherwise adhered to the first surface 14 of the sewing ring frame 12 so that the locking mechanism 22 is accessible to the clinician once the attachment device 10 is mounted to the patient's heart. Having the locking mechanism 22 on the first surface 14 also allows the second surface 16 of the sewing ring frame to lie flat or flush with the heart, which may prevent blood from leaking out or escaping from the heart and into the patient's body rather than being received by the blood pump 24. In the present embodiment, the locking mechanism 22 includes a pull tab or flange 28 projecting from the outer perimeter 20 of the sewing ring frame 12 and a retractable locking pin 30 projecting towards the inner surface 18 of the sewing ring frame 12. The flange 28 may be coupled to the locking pin 30 and a biasing element 32.

Referring now to FIGS. 1-3, the biasing element 32 may be formed of an elastomeric material or spring which allows the biasing element 32 to become compressed when a user applies a pulling force to the flange 28, and return to its original position once the pulling force is released. In a non-limiting example, the flange 28 may be an outwardly projecting flat rim, tab, collar, ridge, or rim of an object that encompasses the biasing element 32 and is configured to be grasped by the clinician so that the pulling force may be applied to the biasing element 32 to retract the locking pin 30. Pulling the flange 28 causes the biasing element 32 to become compressed, which in turn retracts the locking pin 30. In a non-limiting example, the locking pin 30 may be a rod, lever, nail, tack, or the like, sized to fit between the biasing element 32 and the inner surface 18 of the sewing ring frame 12. Further, as shown in FIGS. 2-4, when the biasing element 32 is engaged by the pulling of the flange 28, the biasing element 32 and locking pin 30 may be transitionable between a first unlocked configuration and a second locked configuration.

Continuing to refer to FIG. 2, which shows the locking mechanism 22 in an unlocked configuration in which the locking pin 30 is in a disengaged position and is retracted towards the biasing element 32 and flange 28. The locking pin 30 is in the unlocked configuration when the user pulls the flange 28. When the flange 28 is pulled, the biasing element 32 is compressed, allowing for the insertion of an inflow cannula 34 through an aperture 36 and into a cored hole of the heart. Full insertion of the inflow cannula 34 may require the locking pin 30 to be retracted until an attachment or inflow ring 38 is positioned to fit within the aperture 36 defined by the inner surface 18 of the sewing ring frame 12. The inflow ring 38 may be attached to the inflow cannula 34 of the blood pump 24. The inflow ring 38 is generally sized and shaped so that it can be easily position within the aperture 36.

Figure 4:
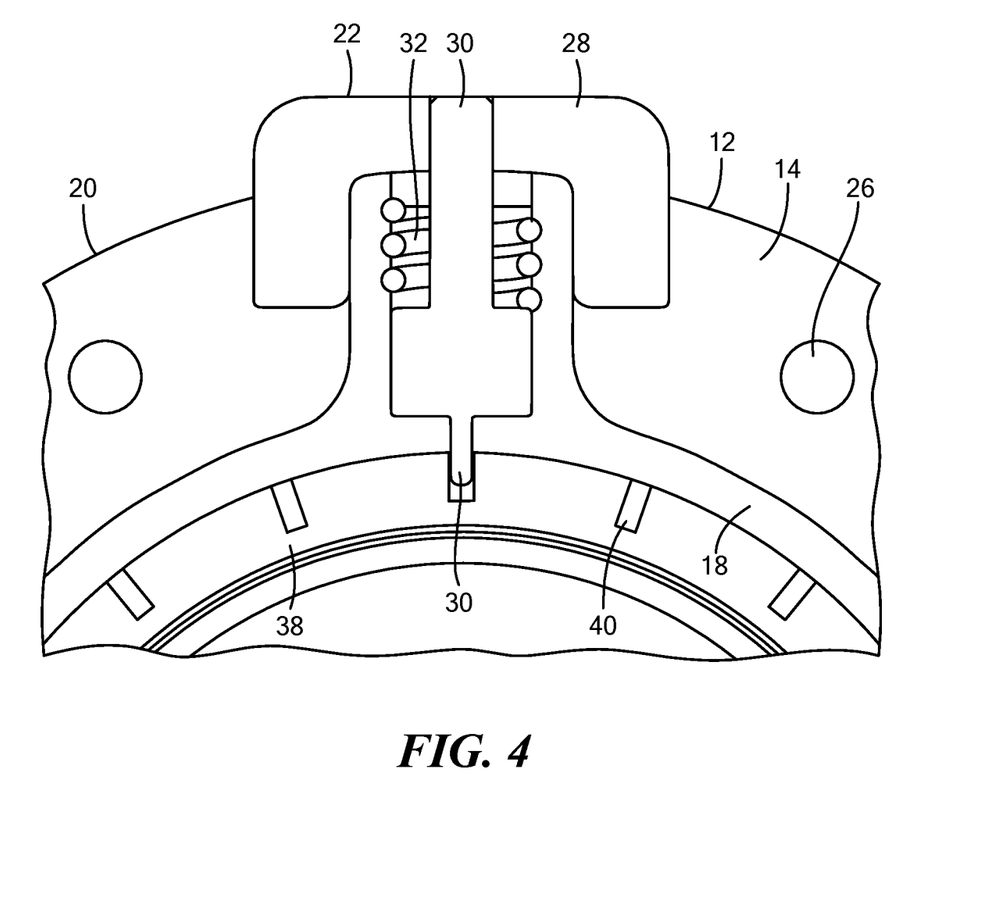
FIG. 4 is a closer perspective view of FIG. 3, wherein the locking pin of the locking mechanism engages a corresponding mating member of the inflow ring.
Figure 5:
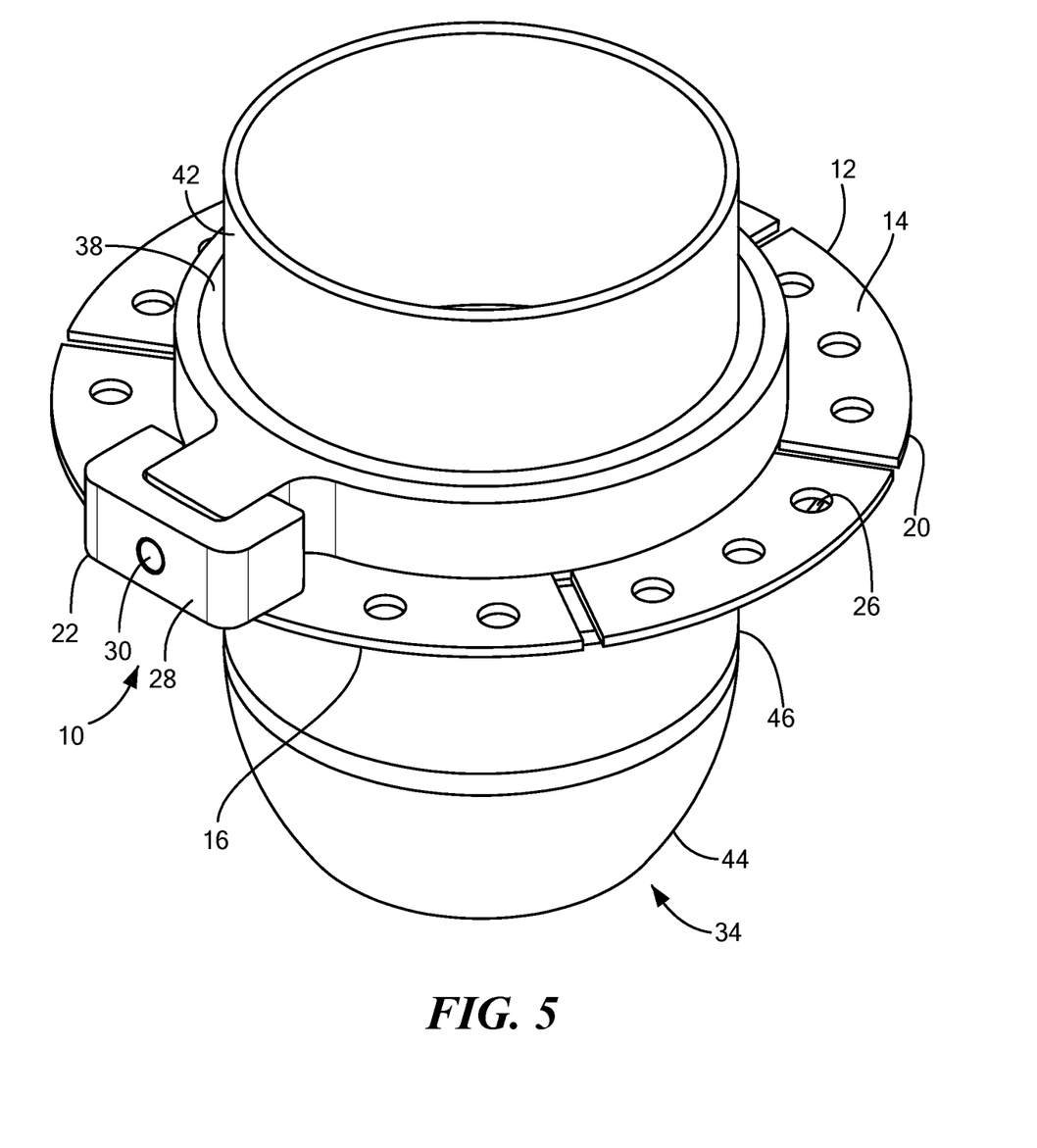
FIG. 5 is a side view of the if the invention of FIG. 1 illustrating the completed attachment of the attachment device to the inflow cannula of the blood pump.

Referring now to FIGS. 3-5, the locking pin 30, for example, may be a mating member configured to engage a corresponding mating member 40 of the blood pump 24. As a non-limiting example, the corresponding mating member 40 may be at least one detent, slot, hole, or small opening sized and configured to receive the locking pin 30 of the attachment device 10. Additionally, the inflow cannula 34 has a proximal and distal portion 42, 44. The corresponding mating member 40 may be located on the inflow ring 38 that is attached to the proximal portion 42 of the inflow cannula 34 of the blood pump 24. As shown in FIG. 5, the aperture 36 defined by the sewing ring frame 12 is sized to at least partially receive the distal portion 44 of the inflow cannula 34 through the first surface 14 of the sewing ring frame 12. When the inflow cannula 34 is fully inserted through the aperture 36, the inflow ring 38 may be flush with the inner surface 18 of the sewing ring frame 12. This particular positioning of the inflow ring 38 allows for the engagement of the locking pin 30 and the corresponding mating member 40 located on the inflow ring 38.

Prior to the insertion of the inflow cannula 34 into the aperture 36, the clinician may "pull" the flange 28 which causes the locking pin 30 to retract and enter its unlocked state. Once the inflow cannula 34 of the blood pump 24 is fully inserted into the aperture 36, the clinician may release the flange 28 causing the biasing element 32 to decompress and the locking pin 30 to extend towards the aperture 36 and engage the corresponding mating member 40. Once the locking pin 30 engages the mating member 40, the attachment device 10 is releasably attached to the blood pump 24. The locking mechanism 22 secures or "locks" the blood pump 24 to the attachment device 10 in such a manner that it may prevent rotational displacement of the blood pump 24 and therefore minimizes the possibility of blood from the heart leaking out into the patient's body.

Referring now to FIGS. 5-6, the inflow cannula 34 further includes a lateral surface 46 extending between the proximal portion 42 and distal portion 44. When the attachment device 10 is releasably attached to the blood pump 24, the sewing ring frame 12 may be distal to the distal portion 44 of the inflow cannula 34 and proximate to a proximal portion 48 of a housing unit 50 of the blood pump 24. In this embodiment, the housing unit 50 may appear to lie on top of the first surface 14 of the sewing ring frame 12. Further, the ideal inflow cannula may be an inflow cannula sized and configured to form an "air-tight" seal when the inflow cannula is inserted through the aperture 36. The formed seal prevents blood from leaking out or escaping from the heart as the blood is being pumped by the blood pump 24. In addition to the proximal portion 48, the housing unit 50 also has a distal portion 52 and an outflow cannula 54. The outflow cannula 54 pumps the received blood from the patient's heart throughout the rest of the patient's body.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system comprising:
   a sewing ring frame having a first surface, a second surface, an inner surface, and an outer perimeter, the inner surface defining an aperture sized to receive an inflow cannula of an implantable blood pump; and
   a locking mechanism mounted to the first surface of the sewing ring frame,
   the locking mechanism including a flange proximate to the outer perimeter, a locking pin proximate to the aperture and distal to the flange, and a biasing element disposed between the flange and the locking pin, the flange being coupled to the biasing element and the locking pin, the flange projecting from the outer perimeter of the sewing ring frame, and the locking pin projecting from the inner surface toward the aperture, the locking mechanism being further configured to transition between a locked configuration and an unlocked configuration; and
   the implantable blood pump, the implantable blood pump including an attachment ring disposed on the inflow cannula, the attachment ring including a corresponding mating member configured to be engaged by the locking pin,
   wherein the locking pin is configured to engage the corresponding mating member in the locked configuration, and
   wherein the locking pin is configured to retract in a direction toward the biasing element and the flange to disengage from the corresponding mating member when the locking mechanism transitions from the locked configuration to the unlocked configuration.

2. The system of claim 1, wherein the sewing ring frame includes at least one slot.

3. The system of claim 1, wherein the biasing element is a spring.

4. The system of claim 1, wherein the locking pin is configured to project from the inner surface toward the aperture when the locking mechanism is in the locked configuration.

5. The system of claim 1, wherein the biasing element is configured to compress when the locking mechanism transitions from the locked configuration to the unlocked configuration.

6. The system of claim 1, wherein the sewing ring frame comprises an apical attachment device.

7. The system of claim 1, wherein the sewing ring frame is made up of a bio-compatible material.

8. A system, comprising:
an apical attachment device including:
a sewing ring frame having a first surface, a second surface, an inner surface, and an outer perimeter, the inner surface defining an aperture sized to receive an inflow cannula of an implantable blood pump; and
a locking mechanism mounted to the first surface of the sewing ring frame, the locking mechanism having a flange proximate to the outer perimeter, a locking pin proximate to the aperture and distal to the flange, and a biasing element disposed between the flange and the locking pin, the flange being coupled to the biasing element and the locking pin, the flange projecting from the outer perimeter of the sewing ring frame, and the locking pin projecting from the inner surface towards the aperture; and
the implantable blood pump, the implantable blood pump including an attachment ring disposed on the inflow cannula, the attachment ring including a corresponding mating member configured to be engaged by the locking pin to secure the implantable blood pump to the apical attachment device.

9. The system of claim 8, wherein the sewing ring frame includes at least one slot.

10. The system of claim 8, wherein the biasing element is a spring.

11. The system of claim 8, wherein the corresponding mating member includes at least one detent.

12. The system of claim 11, wherein the at least one detent is circumferentially disposed around the attachment ring.

13. The system of claim 8, wherein the locking pin is configured to project from the inner surface of the sewing ring frame and toward the aperture when the locking mechanism is in a locked configuration.

14. The system of claim 8, wherein the locking pin is configured to retract in a direction toward the biasing element and the flange.

15. The system of claim 8, wherein the locking mechanism is configured to transition between a locked configuration and an unlocked configuration, wherein the locking pin is configured to engage the corresponding mating member in the locked configuration, and wherein the locking pin is configured to disengage from the corresponding mating member in the unlocked configuration.

16. The system of claim 15, wherein the locking mechanism is configured to transition from the locked configuration to the unlocked configuration when a pulling force is applied to the flange.

17. The system of claim 15, wherein the biasing element is configured to compress when the locking mechanism transitions from the locked configuration to the unlocked configuration.

18. The system of claim 8, wherein the engagement of the locking pin to the corresponding mating member prevents rotational displacement of the implantable blood pump when the locking pin secures the implantable blood pump to the apical attachment device.

19. The system of claim 8, wherein the implantable blood pump is a Left Ventricular Assist Device (LVAD).

20. A system comprising:
an attachment device including:
a sewing ring frame having a first surface, a second surface, an inner surface, and an outer perimeter, the inner surface defining an aperture sized to receive an inflow cannula of a Left Ventricular Assist Device (LVAD); and
a locking mechanism mounted to the first surface of the sewing ring frame, the locking mechanism including:
a flange proximate to the outer perimeter;
a locking pin proximate to the aperture and distal to the flange; and
a spring biasing element disposed between the flange and the locking pin, the flange being coupled to the spring biasing element and the locking pin, the flange projecting from the outer perimeter of the sewing ring frame, and the locking mechanism configured to transition between a locked position and an unlocked configuration when a pulling force is applied to the flange; and
the LVAD including:
the inflow cannula having a proximal portion and a distal portion; and
an attachment ring attached to the proximal portion of the inflow cannula, the attachment ring including at least one detent,
wherein the locking pin is configured to project from the inner surface toward the aperture to lockingly engage the at least one detent to secure the LVAD to the attachment device, and
wherein the engagement of the locking pin and the at least one detent prevents rotational displacement of the LVAD.

* * * * *